United States Patent
Rezvani

(10) Patent No.: US 6,414,493 B1
(45) Date of Patent: Jul. 2, 2002

(54) TOROID CONDUCTIVITY SENSOR

(75) Inventor: Behzad Rezvani, Anaheim, CA (US)

(73) Assignee: Rosemount Analytical Inc., Irvine, CA (US)

( * ) Notice: Subject to any disclaimer, the term of this patent is extended or adjusted under 35 U.S.C. 154(b) by 0 days.

(21) Appl. No.: 09/817,811

(22) Filed: Mar. 26, 2001

(51) Int. Cl.[7] .............................................. G01N 27/02
(52) U.S. Cl. ...................................... 324/442; 324/449
(58) Field of Search ................................ 324/445, 446, 324/447, 437, 442

(56) References Cited

U.S. PATENT DOCUMENTS

| | | | |
|---|---|---|---|
| 5,077,525 A | * 12/1991 | West et al. ................. | 324/445 |
| 5,334,940 A | 8/1994 | Blades ........................ | 324/442 |
| 5,455,513 A | * 10/1995 | Brown et al. ................ | 324/445 |
| 5,793,214 A | * 8/1998 | Wakamatsu .................. | 324/445 |

FOREIGN PATENT DOCUMENTS

EP     0 999 441 A1     10/1999

* cited by examiner

*Primary Examiner*—Jessica Han
*Assistant Examiner*—Lawrence Luk
(74) *Attorney, Agent, or Firm*—Westman, Champlin & Kelly, P.A.

(57) ABSTRACT

A inductive conductivity sensor for measuring conductivity of a fluid includes a housing supporting a controlled impedance loop and a transducer. The transducer includes a driver for inducing a first current into the fluid adjacent the housing, and for inducing a second current into the controlled impedance loop. The transducer further includes a detector for inductively measuring the first and second currents.

20 Claims, 2 Drawing Sheets

US 6,414,493 B1

TOROID CONDUCTIVITY SENSOR

FIELD OF THE INVENTION

This invention relates to inductive conductivity sensors for measuring conductivity of a sample fluid, and particularly to inductive conductivity sensors having a diagnostic resistor in parallel with a current path in the fluid.

BACKGROUND OF THE INVENTION

Inductive conductivity sensors are used for measuring the conductivity of a fluid, such as a liquid or dispersion of solids suspended in the liquid. Inductive conductivity sensors are used to investigate the properties of electrolytes in the fluid, such as the degree of disassociation, the formation of chemical complexes, and hydrolysis.

A toroid inductive sensor is a common form of inductive conductivity sensor that employs two spaced-apart "toroid" transformer coils. A drive coil is electrically excited by an alternating current source to generate a changing magnetic field. The changing magnetic field induces a current loop in the sample fluid; the magnitude of the induced current is indicative of the conductivity of the fluid. A detection coil inductively detects the magnitude of the induced current and provides a measure of the conductivity of the fluid. The body of a toroid sensor is typically cylindrical, and the coils are positioned near opposite ends of the cylinder. The axial passage of the cylinder defines part of the induced current loop in the fluid.

One problem associated with inductive conductivity sensors is that an open circuit condition in either the drive or detection coil circuits is difficult to detect. More particularly, an open circuit condition in the drive coil circuit results in no current being induced in the fluid. However, ion content of the fluid may generate noise in the detection coil that may be mis-analyzed as a conductivity value. An open circuit condition in the detection coil circuit results in no current being supplied to the analyzer from the detection coil, which might be mis-analyzed as a highly resistive (zero conductivity) fluid. The present invention is directed to a technique that permits diagnostics to be performed on the sensor to detect an open circuit condition in either the drive or detection coil electronics.

SUMMARY OF THE INVENTION

An inductive conductivity sensor for measuring conductivity of a fluid includes a housing arranged to be positioned adjacent the fluid. The housing supports a controlled impedance loop and a transducer. The transducer includes a driver arranged to induce a first current into fluid adjacent the housing and to induce a second current into the controlled impedance loop. The transducer also includes a detector arranged to inductively measure the first and second currents.

The current measured by the detector comprises the current representative of solution conductance (the first current) offset by the induced in the controlled impedance loop (the second current). The offset or second current provides the advantage of sensing open circuit in the sensor circuits, as well as to offset the detector current to overcome noise.

In some embodiments, the controlled impedance loop includes a conductive wire inductively coupled to the driver and the detector and a resistor coupled to the conductive wire.

In one form of the invention, the driver includes a first magnetic core adjacent a first end of the housing and a first coil arranged around the first core. Similarly, the detector includes a second magnetic core adjacent a second end of the housing and a second coil arranged around the second core. The controlled impedance loop extends through the first and second cores.

DETAILED DESCRIPTION OF THE PREFERRED EMBODIMENTS

In one form, known as an insertion toroid conductivity sensor, the sensor is immersed in the fluid whose conductivity is to be measured. One example of an insertion sensor is one that is inserted into a pipe or conduit through which the fluid is flowing. The insertion toroid conductivity sensor measures conductivity of the fluid flowing in the conduit. Another form of toroid conductivity sensor is known as a flow-through toroid conductivity sensor in which the conduit carrying the fluid is in an axial passage through the sensor. The principal difference between the two types of sensors is that the drive and detection coils and circuits of the insertion-type sensor must be protected from corrosive fluids being measured, whereas the coils and circuits of the flow-through type sensor do not.

Figure 1:
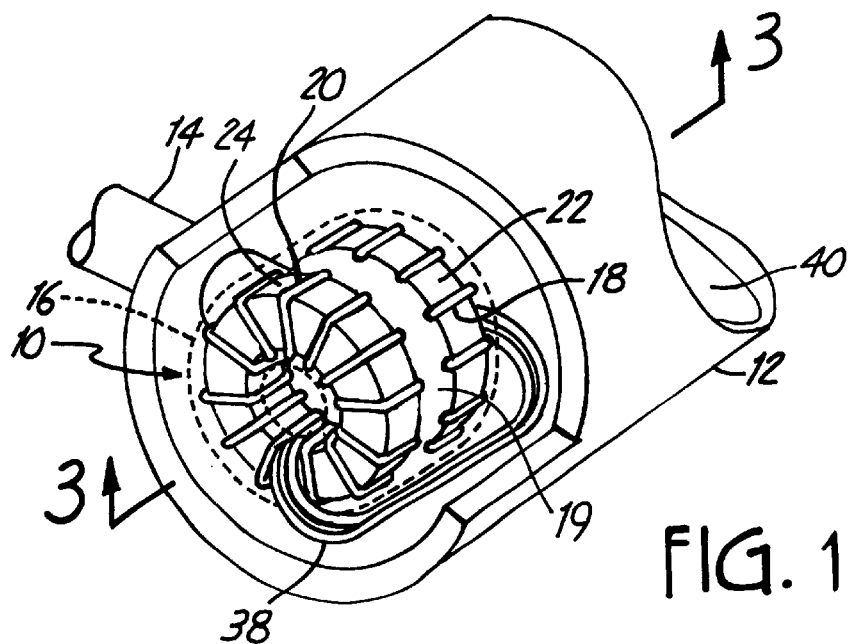
FIG. 1 is a perspective view of an inductive conductivity sensor mounted within a conduit according to a first embodiment of the present invention.
Figure 2:
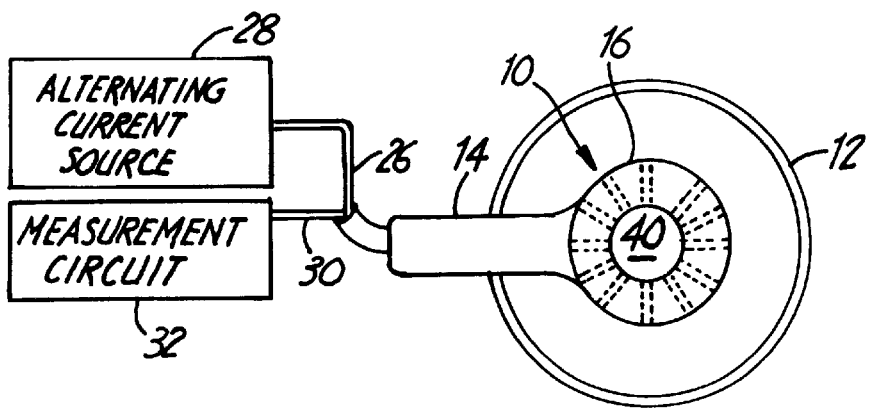
FIG. 2 is a side view of the sensor shown in FIG. 1 coupled to a power source and measurement circuit.
Figure 3:
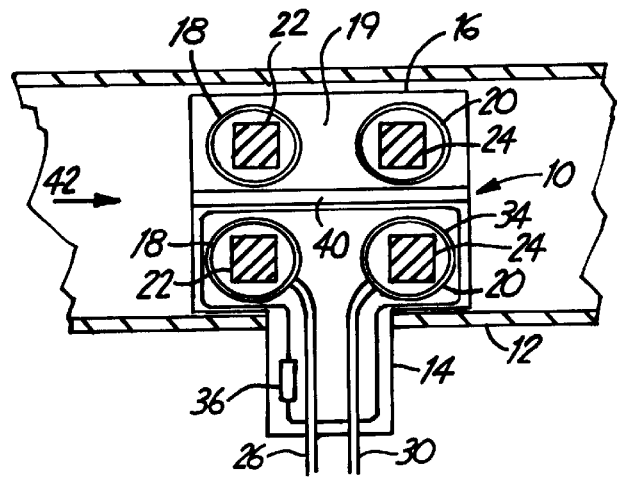
FIG. 3 is a section view of the sensor shown in FIG. 1 taken at line 3—3 in FIG. 1.

FIGS. 1–3 illustrate an insertion toroid inductive conductivity sensor 10 according to one embodiment of the present invention. Sensor 10 is mounted inside conduit 12 carrying the fluid 42 whose conductivity is to be measured. Body 16 includes an arm or strut 14 that is mounted to a wall of the conduit to support body 16 within the conduit. Alternatively, sensor 10 may be mounted to the wall of a tank or other container, such as in a chemical process stream. Sensor 10 is an insertion-type sensor, so named because the body 16 of the sensor is inserted directly into the conduit or container for the fluid whose conductivity is being measured. Thus, sensor 10 is in direct contact with the fluid.

Body 16 encloses and supports first and second toroidal coils 18 and 20 comprising electrical wires wrapped around respective toroidal ferromagnetic cores 22 and 24. Body 16, which is shown in phantom in FIG. 1 for sake of clarity, is constructed of non-magnetic, non-conductive material, and forms a non-magnetic region 19 between the regions of cores 22 and 24. Coil 18 is a driver coil and is electrically coupled by wires 26 to an alternating current source 28 (FIG. 2). Coil 20 is a pick-up coil and is electrically coupled by wires 30 to a measurement circuit 32 (FIG. 2).

As shown particularly in FIG. 3, wire 34 is supported within body 16 and forms a continuous conductive loop through coils 18 and 20. The loop formed by wire 34 includes resistor 36. In the embodiment shown in FIGS. 1–3, body 16 is arranged to be supported within conduit 12 carrying the fluid whose conductivity is to be measured.

Consequently, coils 18 and 20 and wire 34 are protected from any corrosive nature of the fluid being measured by the material of body 16.

In operation of the toroid inductive conductivity sensor of FIGS. 1–3, application of an alternating current to coil 18 generates an alternating magnetic field within magnetic core 22. This magnetic field induces an alternating current in the fluid, represented by loop 38. The electrical resistance of fluid 42 impedes current flow in loop 38. At the same time, the magnetic field in core 22 induces an alternating current in the loop formed by wire 34. The resistance value of fixed resistor 36 impedes current flow in wire 34. The flows of current in wire 34 and in loop 38 induce an alternating magnetic field in magnetic core 24, which in turn induces an alternating current in coil 20. The current induced in coil 20 is measured by circuit 32.

Figure 4:
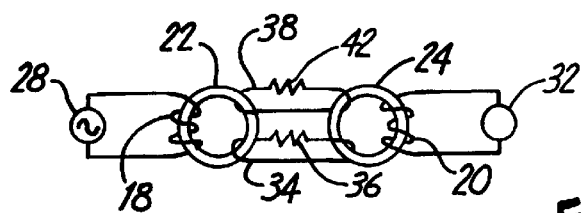
FIG. 4 is an equivalent circuit of a sensor coupled to a power source and measurement circuit employing the principles of the present invention.

The equivalent circuit of the sensor is illustrated in FIG. 4. It will be appreciated by those skilled in the art that the fluid resistance 42 and fixed resistor 36 are electrically in parallel. Consequently, the current, $I_{20}$, induced in coil 20 is proportional to the sum of the inverse of the resistances $$\left(I_{20} \propto \frac{1}{R_{42}} + \frac{1}{R_{36}}\right).$$

The current induced in wire 34 is in parallel with the current induced in the fluid (loop 38). Consequently wire 34 and its resistor 36 provide a base output in pick-up coil 20 indicative of a closed circuit. While resistor 36 represents an impedance in parallel with the resistivity of the fluid being measured, the effects of the resistor can be electronically offset in measurement circuit 32. By calibrating the measurement circuit to provide a zero readout due solely to the resistor 36, the measurement circuit will provide an output representative solely of the resistivity (conductivity) of the fluid. If an open circuit condition occurs in either the drive circuit of source 28 and coil 18 or the detection circuit of coil 20 and measurement circuit 32, the absence of the resistor 36 in the induction loop causes the measurement circuit to provide a negative output, indicative of the open circuit.

Another feature of the present invention resides in the fact that the controlled impedance loop provides a current to the detector to offset the sense current through the solution. If the solution has a high impedance (low conductance), the current through the solution, $I_{42}$, will be low. In prior systems, noise induced in the detector current $I_{20}$ could adversely affect the ability to measure low solution currents. The offset of the low solution current to a higher detection current due to the loop of conductor 34 and resistor 36 diminishes the effect of noise.

Figure 5:
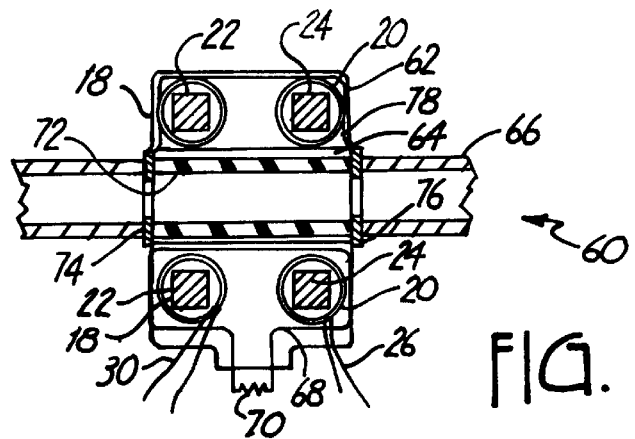
FIG. 5 is a section view of an inductive conductivity sensor according to a second embodiment of the present invention.

FIG. 5 illustrates a second embodiment of a sensor 60 according to the present invention. In this case, sensor 60 is a flow-through toroid inductive conductivity sensor that includes a body 62 having an axial passage 64 for receiving conduit 66 carrying the fluid whose conductivity is to be measured. Conduit 66 includes a non-conductive section 72 and conductive washers 74 and 76 at each end of body 62 in contact with the fluid in conduit 66. Wire 78 is coupled to washers 74 and 76 to complete a loop circuit around cores 22 and 24 for current flowing in the solution in conduit 66. Coils 18 and 20 are coupled to ferromagnetic cores 22 and 24 which in turn are supported by body 62. Wires 26 and 30 couple coils 18 and 20 to the source of alternating current and measurement circuits, as in the case of the sensor of FIGS. 1–3. Wire 68 forms a loop through cores 22 and 24 and includes a fixed resistor 70.

Sensor 60 illustrated in FIG. 5 operates in the same manner as sensor 10 shown in FIGS. 1–3. In this case, however, the fluid is carried by conduit 66 and is not in contact with sensor 60. Consequently, it is not necessary to protect the drive and detection circuits of coils 18 and 20, wires 26 and 30, and cores 22 and 24 from the fluid being measured. Likewise, it is not necessary to protect wire 68 or resistor 70 from the fluid. In this case, it may be advantageous to employ an external resistor 70 that might be changed for different applications of sensor 60.

Although the present invention has been described with reference to preferred embodiments, workers skilled in the art will recognize that changes may be made in form and detail without departing from the spirit and scope of the invention.

What is claimed is:

1. An inductive conductivity sensor for measuring conductivity of a fluid, comprising:
    a housing arranged to be positioned adjacent the fluid;
    a controlled impedance loop supported by the housing; and
    a transducer supported by the housing, the transducer including:
        a driver for inducing a first current into fluid adjacent the housing and for inducing a second current into the controlled impedance loop; and
        a detector for inductively measuring the first and second currents.

2. The sensor of claim 1, wherein the controlled impedance loop provides a diagnostic function so that absence of detecting the second current by the detector is representative of an open circuit of the sensor.

3. The sensor of claim 1, wherein the second current provides an offset of the first current for the detector to minimize effects of noise in the first current.

4. The sensor of claim 1, wherein the controlled impedance loop includes
    a conductive wire inductively coupled to the driver and the detector, and
    a predetermined impedance coupled to the conductive wire.

5. The sensor of claim 1, wherein the driver includes a first magnetic core adjacent a first end of the housing and a first coil arranged around the first core, and wherein the detector includes a second magnetic core adjacent a second end of the housing and a second coil arranged around the second core, and wherein the controlled impedance loop extends through the first and second cores.

6. The sensor of claim 5, wherein the controlled impedance loop includes
    a conductive wire inductively coupled to the driver and the detector, and
    a predetermined impedance coupled to a conductive wire.

7. The sensor of claim 6, wherein the housing is a substantially cylindrical housing having an axial passage.

8. The sensor of claim 7, wherein the housing is arranged to be positioned in contact with the fluid so that the fluid flows through the axial passage.

9. The sensor of claim 8, wherein the housing encloses the transducer and the controlled impedance loop.

10. The sensor of claim 7, wherein at least a portion of the controlled impedance loop is adjacent the axial passage.

11. The sensor of claim 7, wherein the axial passage is arranged to receive a conduit carrying the fluid.

12. The sensor of claim 1, wherein the housing is a substantially cylindrical housing having an axial passage.

13. The sensor of claim 12, wherein the housing is arranged to be positioned in contact with the fluid so that the fluid flows through the axial passage.

14. The sensor of claim 13, wherein the housing encloses the transducer and the controlled impedance loop.

15. The sensor of claim 12, wherein at least a portion of the controlled impedance loop is adjacent the axial passage.

16. The sensor of claim 12, wherein the axial passage is arranged to receive a conduit carrying the fluid.

17. An inductive conductivity sensor for measuring conductivity of a fluid, comprising:

a substantially cylindrical housing having an axial passage arranged to be positioned adjacent the fluid;

a controlled impedance loop supported by the housing, the controlled impedance loop including:
  a conductive wire, and
  a predetermined impedance coupled to the conductive wire; and a transducer supported by the housing, the transducer including:
  a first magnetic core adjacent a first end of the housing and a first coil arranged around the first core so that a drive current in the first coil induces a magnetic field in the first core which induces a measurement current in the fluid adjacent the first core and induces a base current in the conductive wire; and
  a second core adjacent a second end of the housing and a second coil arranged around the second core detector the second core and second coil being arranged with the fluid and the conductive wire so that measurement current in the fluid and base current in the conductive wire induce a magnetic field in the second core which induces a pickup current in the second coil, the pickup current being based on the conductivity of the fluid and the predetermined impedance.

18. The sensor of claim 17, wherein the controlled impedance loop induces a minimum current in the pickup current.

19. The sensor of claim 17, wherein the housing is arranged to be positioned in contact with the fluid so that the fluid flows through the axial passage.

20. The sensor of claim 17, wherein the axial passage is arranged to receive a conduit carrying the fluid.

* * * * *